US00PP36855P3

(12) United States Plant Patent
Miyawaki

(10) Patent No.: US PP36,855 P3
(45) Date of Patent: Jul. 22, 2025

(54) ***ASPIDISTRA* PLANT NAMED 'HANADO RAKU NO 1'**

(50) Latin Name: *Aspidistra vietnamensis*
Varietal Denomination: HANADO RAKU NO 1

(71) Applicant: Shiro Miyawaki, Tokyo (JP)

(72) Inventor: Shiro Miyawaki, Tokyo (JP)

( * ) Notice: Subject to any disclaimer, the term of this patent is extended or adjusted under 35 U.S.C. 154(b) by 37 days.

(21) Appl. No.: 18/389,276

(22) Filed: Nov. 14, 2023

(65) Prior Publication Data

US 2025/0160231 P1 May 15, 2025

(51) Int. Cl.
*A01H 5/12* (2018.01)
*A01H 6/12* (2018.01)

(52) U.S. Cl.
USPC ..... Plt./373
CPC ..... *A01H 6/12* (2018.05); *A01H 5/12* (2013.01)

(58) Field of Classification Search
USPC ..... Plt./373
See application file for complete search history.

*Primary Examiner* — Susan McCormick Ewoldt

(57) ABSTRACT

A new and distinct *Aspidistra* cultivar named 'HANADO RAKU NO 1' is disclosed, characterized by dark green foliage with abundant stable and distinctive creamy white spots. The new cultivar is an *Aspidistra*, suitable for indoor ornamental and tropical garden purposes.

1 Drawing Sheet

Latin name of the genus and species: *Aspidistra vietnamensis*.
Variety denomination: 'HANADO RAKU NO 1'.

BACKGROUND OF THE INVENTION

The new cultivar is a product of chance discovery by the inventor, at a commercial nursery in Oshima-Machi, Japan during 2007. This new variety, hereinafter referred to as 'HANADO RAKU NO 1', was discovered as a naturally occurring, whole plant mutation of the parent variety *Aspidistra vietnamensis*, 'Amanogawa', unpatented. The new variety was selected in a field of the parent variety at a commercial nursery in Oshima-Machi, Japan.

After identifying the new variety as a potentially interesting selection, the inventor first organized propagation of 'HANADO RAKU NO 1' using division of the rhizome during 2007 at a private commercial nursery in Oshima-Machi, Japan. The inventor continued controlled testing and propagation, assessing stability of the unique characteristics of this variety. Numerous generations have been reproduced and have shown that the unique features of this cultivar are stable and reproduced true to type.

SUMMARY OF THE INVENTION

The cultivar 'HANADO RAKU NO 1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HANADO RAKU NO 1' These characteristics in combination distinguish 'HANADO RAKU NO 1' as a new and distinct *Aspidistra* cultivar:

1. Dark green foliage with abundant stable and distinctive creamy white speckles and short, uneven striations.

COMPARISON TO PARENT VARIETY

The new variety differs from the parent variety in the following:

1. The new variety has dark green foliage with abundant stable creamy white speckles and short, uneven striations; the parent variety has unstable foliage coloration with medium green or dark green foliage with irregular white and light yellow stripes and infrequent minute white spots.

COMMERCIAL COMPARISON

'HANADO RAKU NO 1' can be compared to the commercial variety *Aspidistra elatior* 'Asahi', unpatented. Plants of the new cultivar 'HANADO RAKU NO 1' are similar to plants of 'Asahi' in some horticultural characteristics, however, plants of the new cultivar 'HANADO RAKU NO 1' differ in the following:

1. The new variety has dark green foliage with abundant stable creamy white speckles and short, uneven striations; this comparator has dark green foliage with white aspices.

'HANADO RAKU NO 1' can be compared to the commercial variety *Aspidistra elatior* 'Variegata', unpatented. Plants of the new cultivar 'HANADO RAKU NO 1' are similar to plants of 'Variegata' in most horticultural characteristics, however, plants of the new cultivar 'HANADO RAKU NO 1' differ in the following;

1. The new variety has dark green foliage with abundant stable creamy white speckles and short, uneven striations; this comparator has dark green foliage with white or yellow stripes.

BRIEF DESCRIPTION OF THE PHOTOGRAPH

The accompanying photograph in FIG. 1 illustrates in full color 1-year old plants of the new variety in a 3-inch liner pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HANADO RAKU NO 1' plants grown outdoors in a shade house in Loxley, Alabama. Plants are approximately 4 months old, in a 1-liter nursery container. Measurements and numerical values represent averages of typical plant types.

Botanical classification: *Aspidistra vietnamensis* 'HANADO RAKU NO 1'.

ROOTS

Rhizome description: Moderately thick, very slightly fleshy, fibrous, moderately branched, colored near Yellow-White RHS 158A.

PLANT

Growth habit: Upright. Leaves grow directly from rhizomes, no lateral branches/stems present.
Plant shape: Broad fan-shaped.
Height: Approximately 55 cm to top of highest leaf.
Plant spread: Approximately 30 cm in a 1 liter pot.
Growth rate: Moderate.
Stem: Leaves grow directly from rhizomes, no (lateral) stems present.
Number of leaves per plant: Approximately 7.
Age of plant described: Approximately 4 months.

FOLIAGE

Leaf:
- *Arrangement*.—Leaves grow directly from rhizomes in a somewhat fan-like arrangement.
- *Average length* (*excluding petiole*).—Average range 28 to 45 cm.
- *Average width*.—Average range 6 to 8 cm.
- *Shape of blade*.—Narrow elliptic.
- *Aspect*.—Moderately arched, slightly undulating.
- *Angle*.—Upright.
- *Apex*.—Acute.
- *Base*.—Long acuminate.
- *Margin*.—Entire.
- *Texture of top surface*.—Glabrous. Ribbed.
- *Texture of bottom surface*.—Glabrous. Ribbed. Prominent mid-vein.
- *Appearance*.—Slightly glossy top and bottom surfaces.
- *Color*.—Young foliage upper side: Near RHS Green 137A, irregularly dotted near Yellow-White 158D over about 10 to 20% of leaf surface. Young foliage under side: Near RHS Green 137A, irregularly dotted near Yellow-White 158D over about 10 to 20% of leaf surface. Mature foliage upper side: Near RHS Green 137A, irregularly dotted near Yellow-White 158D over about 30 to 50% of leaf surface. Mature foliage under side: Near RHS Green 137A, irregularly dotted near Yellow-White 158D over about 30 to 50% of leaf surface Venation:
- *Type*.—Linear.
- *Venation coloration upper side*.—Indistinguishable from leaf blade.
- *Venation coloration under side*.—Main vein yellow-green; near 144A, other veins same color as leaf blade, green 137A.

Petiole:
- *Length*.—Approximately 12 to 18 cm.
- *Width*.—About 6 mm to 7 mm.
- *Color*.—Near Green 137A.
- *Strength*.—Very strong.

Geniculum: Not present.

FLOWER

Not observed to date.

OTHER CHARACTERISTICS

Disease and pest resistance: Neither resistance nor susceptibility to normal diseases and pests of *Aspidistra* observed. While *Aspidistra* is not typically susceptible to diseases and pests, potential insect problems include fungus gnats, thrips, root mealybugs and scale. The most common disease is *Sclerotia*.
Temperature tolerance: USDA Zone 10.
Fruit/seed production: Not observed to date.

What is claimed is:

1. A new and distinct cultivar of *Aspidistra* plant named 'HANADO RAKU NO 1' as herein illustrated and described.

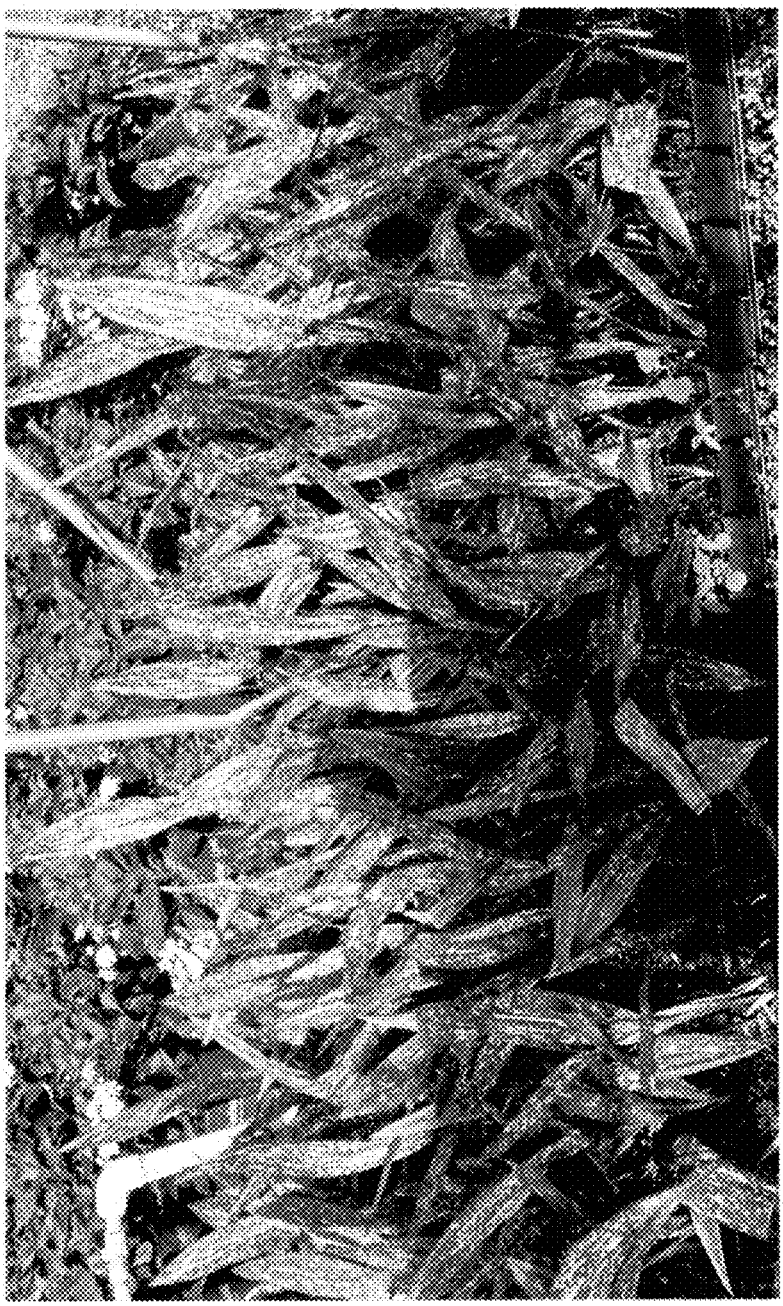

* * * * *